(12) United States Patent
Gokhan

(10) Patent No.: US 7,632,687 B2
(45) Date of Patent: Dec. 15, 2009

(54) HYBRID PHASE LATERAL FLOW ASSAY

(75) Inventor: Cem Gokhan, Frankfurt (DE)

(73) Assignee: Quidel Corporation, San Diego, CA (US)

(*) Notice: Subject to any disclaimer, the term of this patent is extended or adjusted under 35 U.S.C. 154(b) by 263 days.

(21) Appl. No.: 11/088,579

(22) Filed: Mar. 23, 2005

(65) Prior Publication Data

US 2005/0227371 A1    Oct. 13, 2005

Related U.S. Application Data

(63) Continuation-in-part of application No. 10/854,876, filed on May 27, 2004, now abandoned.

(60) Provisional application No. 60/555,612, filed on Mar. 23, 2004.

(51) Int. Cl.
  *G01N 33/53* (2006.01)

(52) U.S. Cl. .......... 436/518; 436/514; 436/169; 436/172; 436/175; 436/530; 436/533; 436/807; 436/170; 436/823; 435/823; 435/805; 435/7.1; 435/7.92; 435/287.7; 422/56; 422/57; 422/58; 422/59; 422/60

(58) Field of Classification Search .......... 436/514, 436/518, 169, 172, 175, 530, 533, 807, 170, 436/823; 435/823, 805, 7.1, 7.92, 287.7; 425/287.7; 422/56–60
See application file for complete search history.

(56) References Cited

U.S. PATENT DOCUMENTS

| | | | |
|---|---|---|---|
| 3,992,158 A | 11/1976 | Przybylowicz et al. | |
| 4,276,149 A | 6/1981 | Litman et al. | |
| 4,299,916 A | 11/1981 | Litman | |
| 4,366,241 A | 12/1982 | Tom | |
| 4,373,932 A | 2/1983 | Gribnau et al. | |
| 4,426,451 A * | 1/1984 | Columbus | 436/518 |
| 4,587,099 A | 5/1986 | Rothe et al. | |
| 4,632,901 A | 12/1986 | Valkirs et al. | |
| 4,643,560 A | 2/1987 | Morse | |
| 4,695,554 A | 9/1987 | O'Connell et al. | |
| 4,702,017 A | 10/1987 | Lenhardt | |
| 4,703,017 A | 10/1987 | Campbell et al. | |

(Continued)

FOREIGN PATENT DOCUMENTS

EP    0249418 A2    9/1987

(Continued)

OTHER PUBLICATIONS

Lindberg, Roy A. "Plastic-Molding Processes", Chapter 10 In *Processes and Materials of Manufacture* 3rd ed., Allyn and Bacon, Boston, (1983) pp. 393-432.

*Primary Examiner*—Bao-Thuy L Nguyen
(74) *Attorney, Agent, or Firm*—Judy M. Mohr; King & Spalding LLP

(57) ABSTRACT

The invention relates to devices for performing single step assays for the determination of the presence or absence of an analyte in a liquid sample, and methods of determining the presence or absence of such analytes using such devices. Devices disclosed comprise a labeled analyte-binding reagent reversibly-immobilized on a non-porous solid material, which solid material is in physical contact with a dry porous carrier bearing an immobilized analyte-binding reagent. Also provided are quantitative assay devices.

22 Claims, 8 Drawing Sheets

U.S. PATENT DOCUMENTS

| | | | |
|---|---|---|---|
| 4,806,311 A | 2/1989 | Greenquist |
| 4,824,640 A | 4/1989 | Hildenbrand et al. |
| 4,863,875 A | 9/1989 | Bailey |
| 4,916,056 A | 4/1990 | Brown, III et al. |
| 4,943,522 A | 7/1990 | Eisinger et al. |
| 4,945,205 A | 7/1990 | Litman et al. |
| 4,999,285 A | 3/1991 | Stiso |
| 5,008,080 A | 4/1991 | Brown, III et al. |
| 5,075,078 A | 12/1991 | Osikowicz et al. |
| 5,096,837 A | 3/1992 | Fan et al. |
| 5,110,550 A | 5/1992 | Schlipfenbacher |
| 5,120,643 A | 6/1992 | Ching et al. |
| 5,145,789 A | 9/1992 | Corti et al. |
| 5,149,622 A | 9/1992 | Brown et al. |
| 5,160,701 A | 11/1992 | Brown, III et al. |
| 5,208,166 A | 5/1993 | Saunders et al. |
| 5,223,220 A | 6/1993 | Fan et al. |
| 5,266,497 A | 11/1993 | Imai et al. |
| 5,275,785 A | 1/1994 | May et al. |
| 5,338,613 A | 8/1994 | Schlipfenbacher et al. |
| 5,356,782 A | 10/1994 | Moorman et al. |
| 5,401,667 A | 3/1995 | Koike |
| 5,415,994 A | 5/1995 | Imrich et al. |
| 5,458,852 A | 10/1995 | Buechler |
| 5,468,647 A | 11/1995 | Skold et al. |
| 5,504,013 A | 4/1996 | Senior |
| 5,516,644 A | 5/1996 | Yamauchi et al. |
| 5,521,102 A | 5/1996 | Boehringer et al. |
| 5,571,726 A | 11/1996 | Brooks, Jr. et al. |
| 5,591,645 A | 1/1997 | Rosenstein |
| 5,602,040 A | 2/1997 | May et al. |
| 5,622,871 A | 4/1997 | May et al. |
| 5,624,809 A | 4/1997 | Skold et al. |
| 5,656,503 A | 8/1997 | May et al. |
| 5,712,170 A | 1/1998 | Kouvonen et al. |
| 5,712,172 A | 1/1998 | Huang et al. |
| 5,714,389 A | 2/1998 | Charlton et al. |
| 5,726,010 A | 3/1998 | Clark |
| 5,766,961 A | 6/1998 | Pawlak et al. |
| 5,770,460 A | 6/1998 | Pawlak et al. |
| 5,773,234 A | 6/1998 | Pronovost et al. |
| 5,786,220 A | 7/1998 | Pronovost et al. |
| 5,804,462 A | 9/1998 | Pronovost et al. |
| 5,877,028 A | 3/1999 | Chandler et al. |
| 5,885,527 A | 3/1999 | Buechler |
| 5,895,765 A | 4/1999 | Rheinheimer et al. |
| 5,965,458 A | 10/1999 | Kouvonen et al. |
| 5,989,921 A | 11/1999 | Charlton et al. |
| 5,998,168 A | 12/1999 | Sugiyama et al. |
| 6,019,944 A | 2/2000 | Buechler |
| 6,057,166 A | 5/2000 | Childs et al. |
| 6,087,184 A | 7/2000 | Magginetti et al. |
| 6,113,855 A | 9/2000 | Buechler |
| 6,143,576 A | 11/2000 | Buechler |
| 6,156,270 A | 12/2000 | Buechler |
| 6,165,798 A | 12/2000 | Brooks |
| 6,180,417 B1 * | 1/2001 | Hajizadeh et al. ........... 436/518 |
| 6,187,268 B1 | 2/2001 | Albarella et al. |
| 6,187,369 B1 | 2/2001 | Beavers |
| 6,194,221 B1 | 2/2001 | Rehg et al. |
| 8,194,222 | 2/2001 | Buechler et al. |
| 6,210,898 B1 | 4/2001 | Bouma et al. |
| 6,228,658 B1 | 5/2001 | Formica et al. |
| 6,228,660 B1 | 5/2001 | May et al. |
| 6,271,040 B1 | 8/2001 | Buechler |
| 6,284,198 B1 | 9/2001 | Kirollos et al. |
| 6,297,060 B1 | 10/2001 | Nowakowski et al. |
| 6,316,205 B1 | 11/2001 | Guan et al. |
| 6,352,852 B1 | 3/2002 | Davis et al. |
| 6,391,265 B1 | 5/2002 | Buechler et al. |
| 6,399,398 B1 | 6/2002 | Cunningham et al. |
| 6,406,920 B1 | 6/2002 | Davis et al. |
| 6,410,341 B1 | 6/2002 | Freitag et al. |
| 6,436,722 B1 | 8/2002 | Clark et al. |
| 6,485,982 B1 | 11/2002 | Charlton |
| 6,534,320 B2 | 3/2003 | Ching et al. |
| 6,605,476 B2 | 8/2003 | Kobayashi |
| 6,656,744 B2 | 12/2003 | Pronovost et al. |
| 6,656,745 B1 | 12/2003 | Cole |
| 6,663,833 B1 | 12/2003 | Stave et al. |
| 6,669,907 B1 | 12/2003 | Buechler |
| 6,673,628 B2 | 1/2004 | Freitag et al. |
| RE38,430 E | 2/2004 | Rosenstein |
| 6,686,170 B1 | 2/2004 | Flanders et al. |
| 6,689,317 B1 | 2/2004 | Rees |
| 6,699,722 B2 | 3/2004 | Bauer et al. |
| 8,737,278 | 5/2004 | Carlsson et al. |
| 6,855,561 B2 | 2/2005 | Jerome et al. |
| 6,924,153 B1 | 8/2005 | Boehringer et al. |
| 2002/0086436 A1 | 7/2002 | Buechler |
| 2002/0098532 A1 | 7/2002 | Chiang |
| 2003/0035758 A1 | 2/2003 | Buechler et al. |
| 2003/0157699 A1 | 8/2003 | Jerome et al. |
| 2003/0161762 A1 | 8/2003 | Caron et al. |
| 2003/0211634 A1 | 11/2003 | Jerome et al. |
| 2004/0077103 A1 | 4/2004 | Buechler |
| 2004/0152207 A1 | 8/2004 | Nelson et al. |

FOREIGN PATENT DOCUMENTS

| | | |
|---|---|---|
| EP | 0258963 A2 | 9/1988 |
| EP | 0353500 A2 | 7/1989 |
| EP | 0260965 A2 | 11/1992 |
| EP | 0383619 B1 | 4/1997 |
| EP | 0903584 A1 | 3/1999 |
| EP | 1248112 A2 | 10/2002 |
| EP | 0833157 B1 | 11/2002 |
| EP | 0291194 B2 | 7/2003 |
| EP | 1327884 A1 | 7/2003 |
| EP | 0901630 B1 | 8/2003 |
| EP | 1376131 A1 | 1/2004 |
| WO | WO 88/08534 | * 11/1988 |
| WO | WO92/21977 A1 | 12/1992 |
| WO | WO95/13542 | 5/1995 |
| WO | WO97/06437 A1 | 2/1997 |
| WO | WO97/26083 A1 | 7/1997 |
| WO | WO97/44664 | 11/1997 |
| WO | WO99/47930 A1 | 9/1999 |
| WO | WO00/63697 A1 | 10/2000 |
| WO | WO01/57522 A2 | 8/2001 |

* cited by examiner

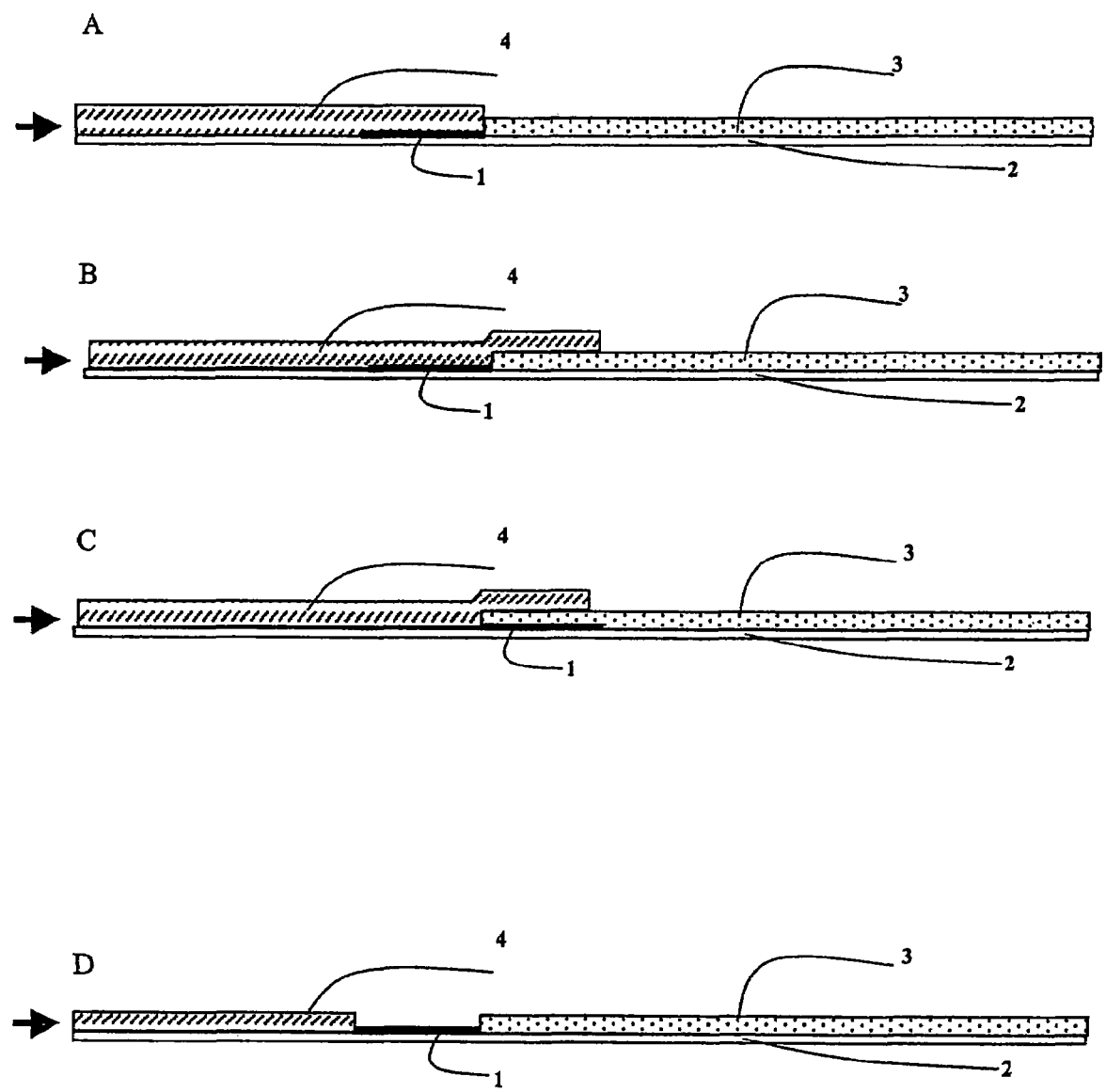
Figure 6: Porous sample reception

Figure 7. Quantitative assay
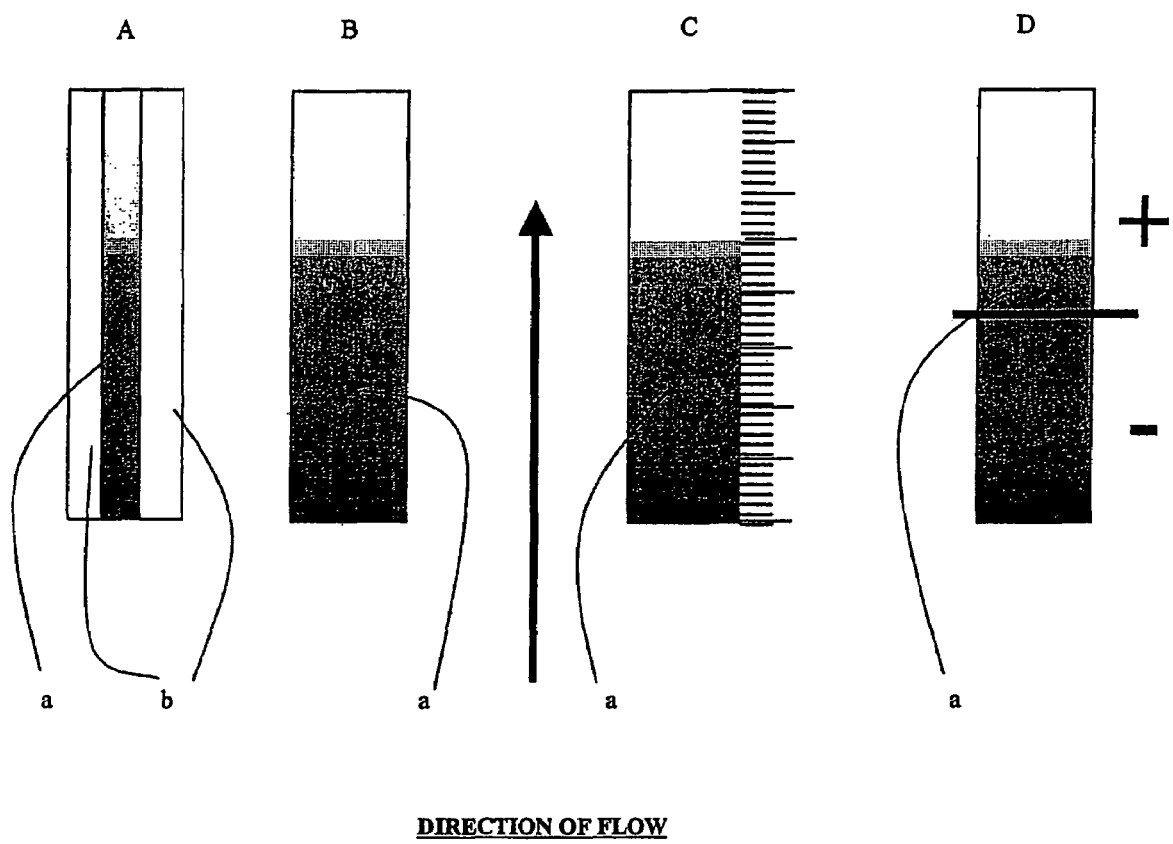
DIRECTION OF FLOW

Figure 8. Quantitative assay
Labeled reagent (e.g., gold-labeled anti-hCG Ab):  
Immobilized capture reagent:   Y
Analyte:   
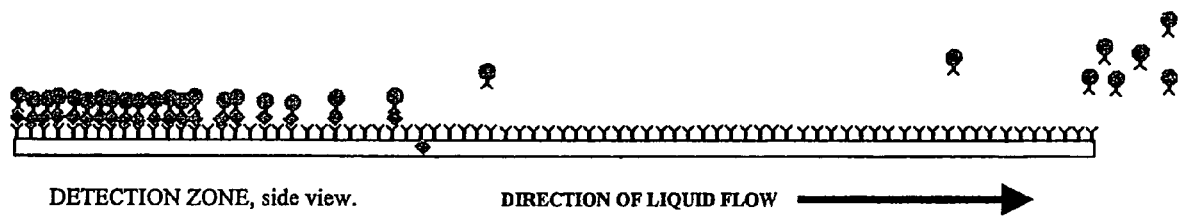
DETECTION ZONE, side view.   DIRECTION OF LIQUID FLOW ⟶

HYBRID PHASE LATERAL FLOW ASSAY

This application is a continuation-in-part of U.S. Non-Provisional application Ser. No. 10/854,876, filed May 27, 2004 now abandoned, which claims the priority of U.S. Provisional Application No. 60/555,612, filed Mar. 23, 2004, the entirety of both applications is incorporated herein by reference.

BACKGROUND OF THE INVENTION

Lateral-flow immunoassays, with their ease of use, speed and reliability, are widely used for self-testing and in the clinical setting. Lateral-flow immunoassays are probably the most common non-electrical method used in rapid medical diagnostics to detect the presence of a specific analyte in a liquid sample.

In the general method, a liquid sample suspected of containing the analyte is applied to a porous carrier. Different porous materials are commonly used for the porous carrier, and can differ in pore size, flow rate, protein-binding specifications and pre-treatment, etc. Essentially, all of the physical activities (e.g., liquid migration) and chemical reactions take place in the porous carrier, in the following order.

First a liquid sample to be tested is introduced to a designated area in the sampling-end (also referred as the "proximal end" or "wet end") of the porous carrier, for a measured time e.g. 5 seconds or in a measured volume e.g. 2 drops. From this point forward, the liquid sample migrates within the porous carrier to the direction of the dry end (also referred as the "distal end"). At the outset of the migration, the liquid sample is frequently optimized for reaction by means of chemicals e.g. pH agents or buffers, surfactants, and/or blockers impregnated into the porous carrier.

Second, while migrating in the porous carrier, the sample mobilizes a labeled reagent that has been reversibly (temporarily) immobilized in the porous carrier. The zone where the mobilizable labeled reagent is located is often referred to as the "labeling zone", but can be referred to as the "reversible immobilization zone" or "mobilization zone"—the terms are equivalent.

Third, while analyte is reacting with the mobilized labeled reagent, the liquid sample and mobilized labeled reagent migrates further within the porous carrier to the detection zone, (which may also be referred to the "irreversible immobilization zone" or merely the "immobilization zone") where reagent that binds the same analyte is fixed or immobilized, usually in the form of a line. When analyte is present in the liquid sample, a "sandwich" in the form of the mobilized labeled reagent:analyte:immobilized reagent is formed, and the resulting concentration of the labeled reagent leads to a visible line appearing in the detection zone, which is indicative of a positive result.

Lastly, remaining sample liquid, together with the rest of the labeled reagent further migrates to a control zone, where a second line appears indicating that sample has progressed through the detection and control zones and that the assay has provided a valid test result. The rest of the sample and the remaining labeled reagent then migrate to a porous sink. Labeled reagent remaining in the porous carrier (other than in the detection zone, control zone or sink) makes up any background signal. In some instances where the migration direction reverses, so called "back flow," occurs. Furthermore, the porous carrier can be pre-treated with chemicals e.g. surfactants.

Lateral-flow immunoassays can also function on the basis of competitive binding of the analyte. In these devices, lack of the test line generally indicates a positive result.

The most common example of a lateral-flow immunoassay device is a pregnancy test. These devices are commonly provided for home use, in a plastic housing with a fibrous or a porous extension, which can be held to a urine stream to collect urine sample into the housing. The urine sample collected this way then migrates to the porous carrier, which contains the labeled reagent and the series of events mentioned above starts. The analyte detected in a pregnancy test is Human Chorionic Gonadotropin (hCG) and the reagents commonly used are anti-hCG monoclonal or polyclonal antibodies. The most common labels are gold or latex particles.

Another known example of a lateral-flow immunoassay device commonly provided for home use is an ovulation test, the analyte being Luteinizing Hormone (LH) and reagents being anti-LH, and the rest of the device being similar to a pregnancy test.

A professional format of lateral-flow immunoassay devices commonly referred to as cassette tests, have smaller housings and a sample application orifice instead of the fibrous extension. The sample orifice exposes part of the porous carrier where a liquid sample can be dispensed with a pipette, directly to the porous carrier.

A low cost format of lateral-flow immunoassay devices is a dipstick test in the shape of a strip.

A diversity of test designs, against an ever increasing number of analytes, especially in the cassette and dipstick format, exists in the market indicating the wide acceptance of the method.

SUMMARY OF THE INVENTION

The present invention provides a new assay, applicable to all known analytes, through a reversible reagent immobilization on a non-porous solid surface and an irreversible reagent immobilization on/in a porous media, wherein non-capillary liquid transport may be achieved on the non-porous solid surface by means of momentum of sampling and/or gravity. The use of a non-porous surface reduces the opportunities for non-specific binding of labeled reagent, thereby facilitating its ready mobilization by applied liquid sample. The increased binding surface area of the porous media enables a higher irreversible immobilization and therefore signal intensity. The use of a minimal number of device components decreases production related complications and the cost, and the use of a non-capillary liquid transport means reduces the residual liquid volume not contributing to the assay chemical reaction and reduces the back-flow.

The present invention also provides improvements in quantitative, dipstick and mid-stream test device designs.

The general reactions between the different analytes, labeled reagents, capture reagents and the control reagents are known to those skilled in art and are not the focus of this invention.

In one aspect, the invention encompasses an analytical test device, which, in the presence of a specific analyte in a liquid sample, is capable of producing a detectable signal, the device is characterized in that it comprises a non-porous solid surface and a porous carrier. The non-porous solid surface comprises a reversibly immobilized labeled reagent against the analyte in a designated reversible immobilization zone, also referred to as mobilization zone or labeling zone, and the porous carrier comprises an immobilized reagent against the analyte in a designated detection zone also referred to as an irreversible immobilization zone, or merely as an immobilization zone. The liquid sample taken into the device can initiate the mobilization of the labeled reagent from the non-porous solid surface, and the labeled reagent-sample mix can move to the detection zone via the porous carrier to produce the signal.

The reversibly immobilized reagent in the reversible immobilization or labeling zone is loosely attached to the non-porous surface such that when sample is applied the reagent releases from the surface and mixes within the sample.

In contrast, the immobilized reagent in the detection, immobilization, or irreversible immobilization zone is designed to remain substantially in place throughout the entire duration of the assay.

In another aspect, the liquid sample, taken into the device, moves along the non-porous surface through the mobilization zone, by non-capillary liquid transport which is achieved by means of momentum sampling and/or gravity means until sample reaches the porous carrier, which then draws the fluid into and over the porous material by capillary or wicking means.

It is a further embodiment of the present invention that either the housing or the bottom surface of the non-porous solid surface include an attached elevation mechanism or foot which causes the device to rest in such a manner that after the liquid sample is applied the liquid sample may flow downhill with the assistance of gravity to draw the liquid sample through the device.

In another embodiment, the device is capable of producing a separate control signal, either in the detection zone or in an additional designated control zone, to confirm the passage of adequate amount of the labeled reagent through the immobilization zone to indicate the completion of the assay and/or the ability of the device to produce the signal in the presence of the analyte.

In other embodiments, the device can have, in addition to the non-porous carrier bearing a reversibly immobilized labeled reagent and a porous carrier bearing an immobilized reagent, any of the numerous aspects of lateral flow assay devices known to those of skill in the art. These include, among others, adaptations that permit the measurement of multiple analytes in the same sample.

In another embodiment, the device comprises two non-porous solid surfaces, positioned parallel to each other, at least one of which comprises the labeled reagent in dry state in the mobilization zone. In a preferred embodiment, the second non-porous surface is sized wider and longer than the first non-porous surface, such that when the second non-porous surface is placed over the first non-porous surface, no edge of the first non-porous surface extends beyond an edge of the second non-porous surface, thus providing improved handling and protection from undesired wetting in midstream sample application. In such a device design, the sample is taken onto the sample reception zone through an orifice in the enlarged non-porous surface.

In an alternately preferred embodiment, the second non-porous surface attached to a device is not sized wider and longer than the first non-porous surface but is the same width and is at least as long as the length of the porous surface and may extend in length from the porous surface either partially or entirely covering the non-porous surface.

In another embodiment, the device comprises a housing with an orifice to intake liquid sample and a window to observe the signal. In a preferred embodiment, at least one element of the housing comprises the labeled reagent in a dry state in the mobilization zone.

It is further preferred that the device in the housing is adapted into various handling accessories, designed for different test applications, such as home use, professional laboratory use and patient side use, wherein the device with a minimum housing is contained in different accessory devices.

The invention further encompasses an analytical test device in the strip format, characterized in that the device comprises two parallel non-porous solid surfaces attached to each other or the continuation of each other or overlap with each other, in the sample receiving end of the device, forming a sample reservoir.

In one embodiment, the reservoir comprises an orifice on either of the non-porous solid surfaces, which may provide means for sample dispensing and ventilation to release the liquid sample from the reservoir.

In one embodiment, the device further comprises a sink, distal to and in fluid contact with the porous carrier, the sink capable of absorbing excess liquid sample after the sample traverses the test strip.

The invention further encompasses a test device, characterized in that the device comprises a housing comprising an evaporation opening for the sink.

The invention further encompasses a test device, characterized in that the device comprises a housing assembled into a second housing or into an accessory device.

The invention further encompasses an analytical test device in the strip format, characterized in that the device comprises two parallel non-porous solid surfaces, one of the said surfaces being absent from part of the sink area thus enabling efficient evaporation.

The invention further encompasses a test strip in a midstream test format, comprising an enlarged solid surface comprising an orifice, the enlarged surface providing protection from undesired wetting during the necessary sampling and handling steps.

The invention further encompasses a test device according to preceding aspects, characterized in that either or both sides of the detection zones are transparent or comprise means to enable the observation of the test result e.g. a window and all above mentioned solid parts, non-porous or porous, can be attached to each other by known techniques such as ultra sonic welding, hot laminating, adhesives or mechanical means.

In another aspect, the invention encompasses an analytical device for the single step determination of the presence of a specific analyte in a liquid sample comprising a test strip comprising: a first piece of non-porous solid surface comprising, in a reversible immobilization zone, a reversibly immobilized labeled reagent that binds the analyte to form a complex; and a porous carrier comprising, in a detection zone, an immobilized reagent that binds the analyte, wherein the porous carrier is in contact with the non-porous solid surface; wherein liquid sample applied to the non-porous solid surface mobilizes the reversibly immobilized labeled reagent, whereupon analyte in the liquid sample is permitted to bind the labeled reagent to form a complex which, together with sample liquid, flows into or onto the porous carrier, wherein the immobilized reagent binds the complex, thereby generating a detectable signal indicative of the presence of the analyte.

In another embodiment, the porous carrier further comprises, at a site separate from and distal to the site of immobilization of the immobilized reagent, a second immobilized binding reagent that binds an agent other than the analyte, and wherein binding of the second immobilized binding reagent to the agent generates a detectable signal that confirms passage of liquid sample to the site separate from and distal to the site of immobilization of the immobilized reagent. In other embodiments, the device is capable of producing a separate control signal, either in the immobilization zone or in an additional designated control zone, to confirm the passage of adequate amount of the labeled reagent through the immobilization zone and/or the ability of the device to produce the signal in the presence of the analyte.

In another embodiment, the device further comprises a porous sample application member. The porous sample application member either overlaps and is in physical contact with the reversibly immobilized reagent on the non-porous solid material, or overlaps and is in physical contact with at least a portion of the porous carrier, which portion overlaps and is in contact with the reversibly immobilized reagent on the non-porous solid material.

In other embodiments, the device can have, in addition to the non-porous carrier bearing a reversibly immobilized labeled reagent and a porous carrier bearing an immobilized reagent, any of the numerous aspects of lateral flow assay devices known to those of skill in the art. These include, without limitation, adaptations that permit the measurement of multiple analytes in the same sample.

In another embodiment, the reversible immobilization or mobilization zone comprises a plurality of labeled reagents. In another embodiment, each of the plurality of labeled reagents binds a different analyte.

In another embodiment, the porous carrier comprises, in the detection zone, a plurality of immobilized binding reagents. In another embodiment, each of the plurality of immobilized binding reagents is located in a spatially distinct site and each binds a different analyte to generate a signal.

In another embodiment, the device further comprises a plurality of the test strip assemblies, each member of the plurality bearing reagents that identify the presence of one or more different analytes.

In another embodiment, the device comprises a second piece of non-porous solid material, sized wider and longer than the first non-porous surface, wherein the second piece of non-porous solid material is positioned parallel to the first piece, the second piece having an aperture through which sample is introduced, and wherein the second piece is positioned such that the aperture is located upstream of the reversible immobilization or mobilization zone and such that the second piece provides protection to the first non-porous surface from undesired wetting during mid-stream sample application.

In another embodiment, the device further comprises a sample reservoir, proximal to the reversible immobilization or mobilization zone and formed from a continuation of the first piece of non-porous solid material or from the juxtaposition of a second piece of non-porous solid material with the first piece of non-porous solid material.

In another embodiment, the device further comprises a housing comprising a non-porous solid material.

In another embodiment, at least one element of the housing constitutes the reversible immobilization or mobilization zone, the zone comprising the reversibly immobilized labeled reagent in a dry state.

In another embodiment, the flow of liquid sample applied to the non-porous solid surface, from the site of application to the reversible immobilization or mobilization zone and subsequently to the porous carrier, is provided by the kinetic force of sample application, such as by mid stream sample application, pipetting, or by a swab.

The invention further encompasses an analytical device for the single step determination of the presence of a specific analyte in a liquid sample comprising a test strip comprising: a) a first piece of non-porous solid material comprising on its surface, in a reversible immobilization or mobilization zone, a reversibly immobilized labeled reagent that binds the analyte; b) a porous carrier comprising, in a detection zone, an immobilized reagent that binds the analyte, wherein the porous carrier is in contact with the non-porous solid surface; and c) a second piece of non-porous solid material, placed over (a) and (b), wherein liquid sample applied to the first non-porous solid material mobilizes the reversibly immobilized labeled reagent, whereupon analyte in the liquid sample is permitted to bind the labeled reagent to form a complex which, together with sample liquid, flows into the porous carrier, wherein the immobilized reagent binds the complex, thereby generating a detectable signal indicative of the presence of the analyte.

In another embodiment, rather than being reversibly immobilized upon the first piece of non-porous solid surface, the labeled reagent is reversibly immobilized in a reversible immobilization or mobilization zone on the surface of the second piece of non-porous solid material that faces the first piece of non-porous material, such that when the test strip assembly is oriented the first piece of non-porous solid material is on the bottom, and the labeled reagent is reversibly immobilized on the underside of the second piece.

It is a further embodiment of the present invention that the detection zone be placed at the proximal portion of the porous carrier, thus being closer to the non-porous mobilization zone.

In another aspect, the invention encompasses a device for the single step quantitative measurement of an analyte in a liquid sample comprising: a) a piece of non-porous solid surface, comprising in a reversible immobilization or mobilization zone, a reversibly immobilized labeled reagent that binds the analyte to form a complex; and b) a strip of porous material, the strip comprising a binding reagent and being in contact with the non-porous solid surface, wherein the binding reagent is applied to and immobilized on the strip of porous material in a detection area having a longitudinal axis parallel to a flow of a liquid sample, wherein when the liquid sample comprises an analyte-label conjugate that is bound by the binding reagent, the binding results in a signal, and wherein the distance from the point at which the liquid sample entered the detection zone to the furthest point in the detection area at which the signal is detected above background is indicative of the amount of analyte present in the sample.

In one embodiment, the detection area is at least 1.5 times as long as it is wide. In another embodiment, the detection area extends over at least 50% of the length of the porous chromatographic material. In another embodiment, the detection area extends over at least 60%, 70%, 80%, 90% or over the full length of the porous material.

In another aspect, the invention encompasses a method of detecting an analyte, the method comprising a) contacting a liquid sample to be tested for said analyte with an analytical device as described herein, and b) permitting the liquid sample to traverse the test strip assembly of the device such that reversibly immobilized, labeled reagent is mobilized and thereafter conveyed to the detection zone of the device, whereat, if analyte is present in the liquid sample, a detectable signal is generated, the signal indicative of the presence of the analyte. Analytical test devices incorporating any or all of the embodiments described above or elsewhere herein can be employed in the analytical methods disclosed herein.

As used herein, the term "test strip" refers to a non-porous solid surface upon which a reversibly immobilized dried reagent is present, and a porous carrier strip with a detection zone which is in contact with the non-porous solid material.

Test strips can additionally have a sink element, and/or a second piece of non-porous solid material overlaid upon the assembly of the first non-porous solid material and the porous carrier. A "test strip" can also include a porous sample receiving element in contact with the non-porous solid material upon which the reversibly immobilized reagent is present. Furthermore, a "test strip" may comprise of one piece of material which through processing or chemical treatment comprises both non-porous and porous physical properties, or multiple pieces including different materials.

As used herein, the term "non-porous" refers to a surface which does not permit liquid sample to enter into or to pass through it under normal assay conditions. A non-porous surface does not absorb liquid sample under normal assay conditions and is non-chromatographic. A non-porous surface is preferably inert, impermeable to humidity and low in protein binding. For a "non-porous" surface as the term is used herein, any pores present are smaller than the smallest reagent used and/or are smaller than any component of the sample. By "smaller than" is meant that the smallest reagent or component of the sample will not pass through any such pore, in any appreciable amount, under liquid flow conditions applied in the routine or optimal operating conditions for the device. "Non-porous" materials can be made of any low protein binding, non-water absorbing, solid material such as thermoform or thermoplastic polymers (e.g. polystyrene, polyethylene, polycarbonate, polypropylene, fluoropolymer, or polyester, or a combination) or glass or metals or ceramics or composite materials well known to those skilled in art. The non-porous surface can also be made of any material which is surface coated with low protein binding, non-water absorbing material e.g. Teflon® fluoropolymer resin or Mylar® polyester film coated cellulose. A porous material, such as certain porous plastics or nitrocellulose, may be made non-porous through pressing or chemical treatment such that the surface is rendered smooth and inert, and reagents and liquids are incapable of penetrating the surface of the "non-porous" material.

As used herein, the term "porous" when used in relation to a porous carrier strip means that the material has pores through which the largest reagents or sample components for a given immunoassay device will pass under liquid flow conditions applied in the routine or optimal operating conditions for the device. The term "porous" refers also to a material with pores which permit or conduct the flow of liquid through the body of the material. It is to be understood that "porous" materials can also permit the flow of liquid across the outer surface of the material, as long as they also permit the passage of the liquid through the body of the material. Porous materials with varying ranges and tolerances of pore size are well known in the art, and include, for example, nitrocellulose, glass fiber, porous plastics, such as polyethylene, and various chromatographic papers, among others.

As used herein, the term "open," when used in reference to a side of a test device assembly, means that an edge is not sealed or adhered to another, such that air or liquid can pass. Thus, an assembly which is "open on at least three sides" has an unsealed opening at an inlet, an outlet and at least one side.

As used herein, the term "overlap" means that when an assembly is viewed from the side, one material, e.g., a sheet of material, extends over top of another. Overlap can but need not necessarily include complete overlap, i.e., the top material covers the full length of the bottom material.

As used herein, the term "at least a portion of said porous carrier," when used in reference to overlap by, e.g., a sample receiving member or element, means that the sample receiving member or element overlaps the porous carrier but does not obscure the detection zone.

As used herein, the term "into," when used in reference to the passage of a liquid sample and materials dispersed within a liquid sample "into" a porous material, means that the sample penetrates a porous material such that it is carried within the pores of the porous material as the liquid sample flows. The term "into" when used in this manner does not exclude the simultaneous passage of liquid sample over the surface of a porous carrier material "into" which the sample is flowing. In preferred aspects, however, the passage of liquid over the surface of the porous carrier material is reduced by the presence of a non-porous backing layer and/or the presence of an additional non-porous material overlaid on the porous carrier material.

As used herein, the term "reversible immobilization" refers to the deposition of a reagent on a non-porous solid surface in a manner such that it is readily solubilized or dispersed by liquid sample as applied to an assay device as described herein. By readily solubilized or dispersed is meant that at least 80%, and preferably at least 90% or even 100% of the reversibly immobilized material is solubilized or dispersed into the liquid by the application of liquid sample under the liquid flow conditions applied in the routine or optimal operating conditions for the device.

As used herein, the term "reversible immobilization zone" refer to the discrete situs on a non-porous solid material at which the labeled reagent is reversibly immobilized. The reversible immobilization zone is also referred to herein as the "mobilization zone," or the "labeling" zone.

By "mobilized" is meant at least the partial dispersal or solubilization of a labeled reagent from the dry, reversibly immobilized state to the mobile state capable of flowing to and through a porous carrier in an assay device as described herein. By "mobile" is meant that the labeled reagent is moving in a lateral direction relative to a surface, for example, the reagent is moving in or with a flowing liquid.

As used herein, the relative terms "proximal" and "distal" are based upon the direction of flow—liquid sample flows from the proximal end of a test strip assembly to the distal end.

As used herein, the term "detection zone" refers to the region or regions on a porous carrier as described herein that comprise immobilized analyte binding reagent, located in one or more discrete locations. The detection zone is proximal to any control zone or zones and proximal to the sink. In the quantitative assay embodiments described herein, the detection zone can extend up to the full length of the porous carrier material.

As used herein, the term "in contact" refers to direct contact between two entities, but also includes the use of intervening structures between entities described herein, so long as there is touching or contact between the elements and/or fluid flow amongst the elements.

As used herein, the term "immobilized," when used in reference to an immobilized reagent (as opposed to a reversibly immobilized reagent) means that the reagent is not appreciably solubilized or displaced by the passage of liquid sample under the liquid flow conditions applied in the routine or optimal operating conditions for the device. By "not appreciably solubilized or displaced" is meant that most of the immobilized reagent remains attached to the porous carrier during and after passage of the liquid sample under normal or routine assay conditions.

As used herein, the term "specifically binds" means that an agent binds with a dissociation constant of 1 µM or less. An agent that "specifically binds" an analyte will preferentially bind that analyte in the presence of a large number of non-related molecules. With regard to binding agents, it will commonly be the situation that both a reversibly immobilized binding reagent and an immobilized binding reagent will specifically and essentially exclusively bind the analyte of interest. However, the reversibly immobilized labeled reagent and the immobilized reagent need not necessarily have specificity for binding only to the analyte of interest. For example, one can use one reagent that binds a class of analytes, for example, on the basis of a structural similarity shared by members of the class, and a second reagent that binds the analyte of interest.

As used herein, the term "spatially distinct" means that the given region is sufficiently separated from another region as to be discerned as separate and non-overlapping by eye. Generally, as the term is used herein with regard to regions on a detection zone, two regions are "spatially distinct" if they are greater than or equal to 0.2 mm apart, e.g., 0.2 mm, 0.3 mm, 0.5 mm, 1.0 mm, etc.

As used herein, the terms "wider" and "longer" mean that a given piece of material, e.g., a sheet of non-porous material, is at least 1 mm greater, and preferably more (e.g., 2 mm, 3 mm, etc.), in width and length than another to which it is being compared.

As used herein, the term "midstream sample application" refers to the application of liquid sample by holding the assay device in the flow of a liquid, e.g., in the flow of urine during urination.

As used herein, the term "sample reservoir" refers to an element of an assay device as described herein that can hold liquid sample at least sufficient to permit an assay device to provide a test result. A sample reservoir will generally be located at the proximal end of the assay device, such that application of liquid sample to the reservoir will result in application of liquid sample to the non-porous solid surface near the reversible immobilization or mobilization zone.

As used herein, a "housing" is a casing surrounding at least the detection zone of an assay device described herein—the housing will have at least an aperture for the addition of sample, and for the observation of a test result. An aperture to permit evaporation, e.g., from a sink, can also be present. It is preferred where a housing is used, that the housing be an active member in the assay device, e.g., by providing as a surface for reversible mobilization and/or the immobilization zone.

As used herein, the term "detected above background" means that a given signal is greater than the amount of signal one would obtain in an assay run in the absence of analyte.

BRIEF DESCRIPTION OF THE DRAWINGS

The drawings are not to scale.

Drawing 1 shows one embodiment of the devices described herein. Drawing 1A shows the assembled device and Drawing 1B shows the unassembled device.

Figure 1:
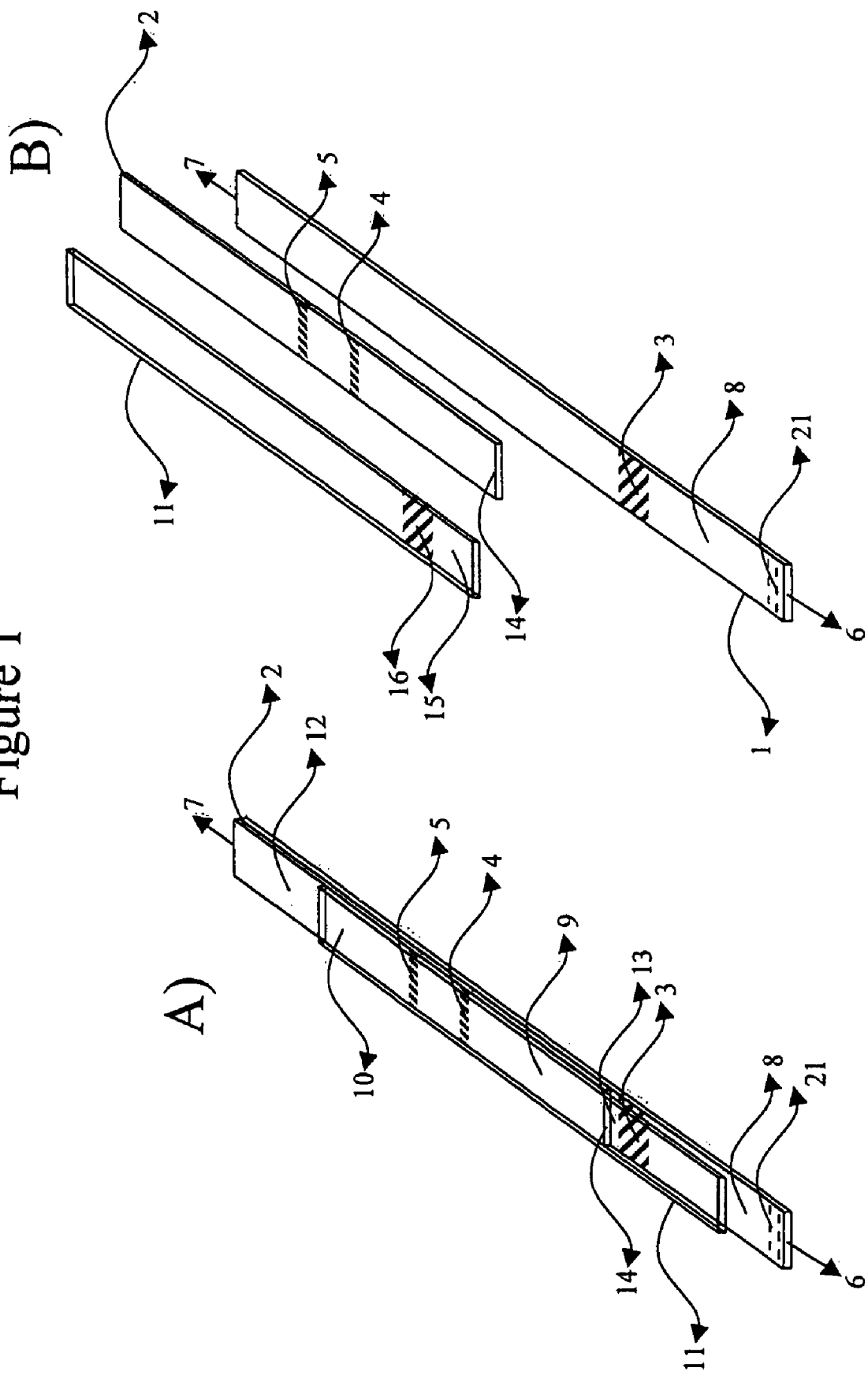
Figure 2:
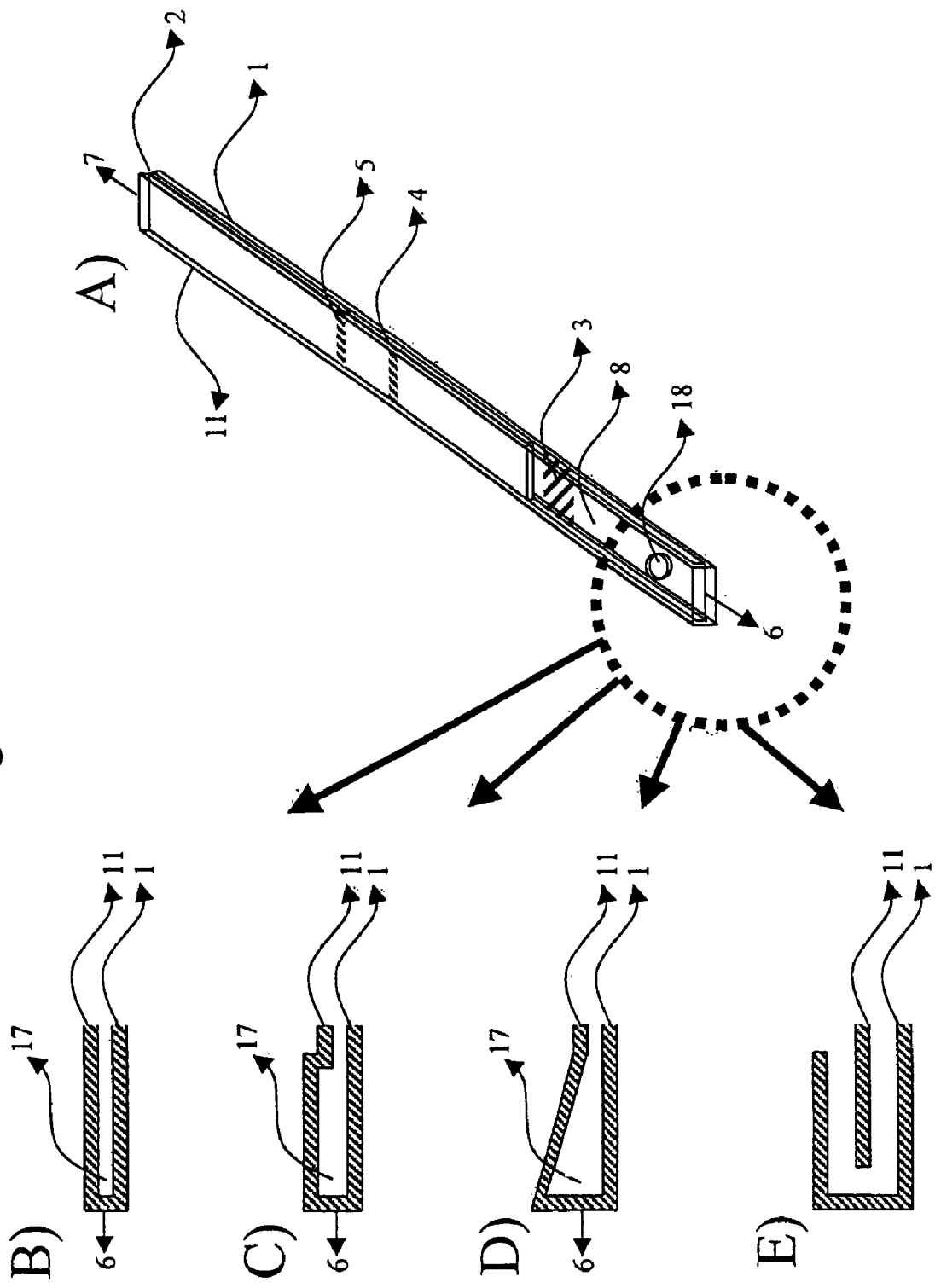
Figure 3:
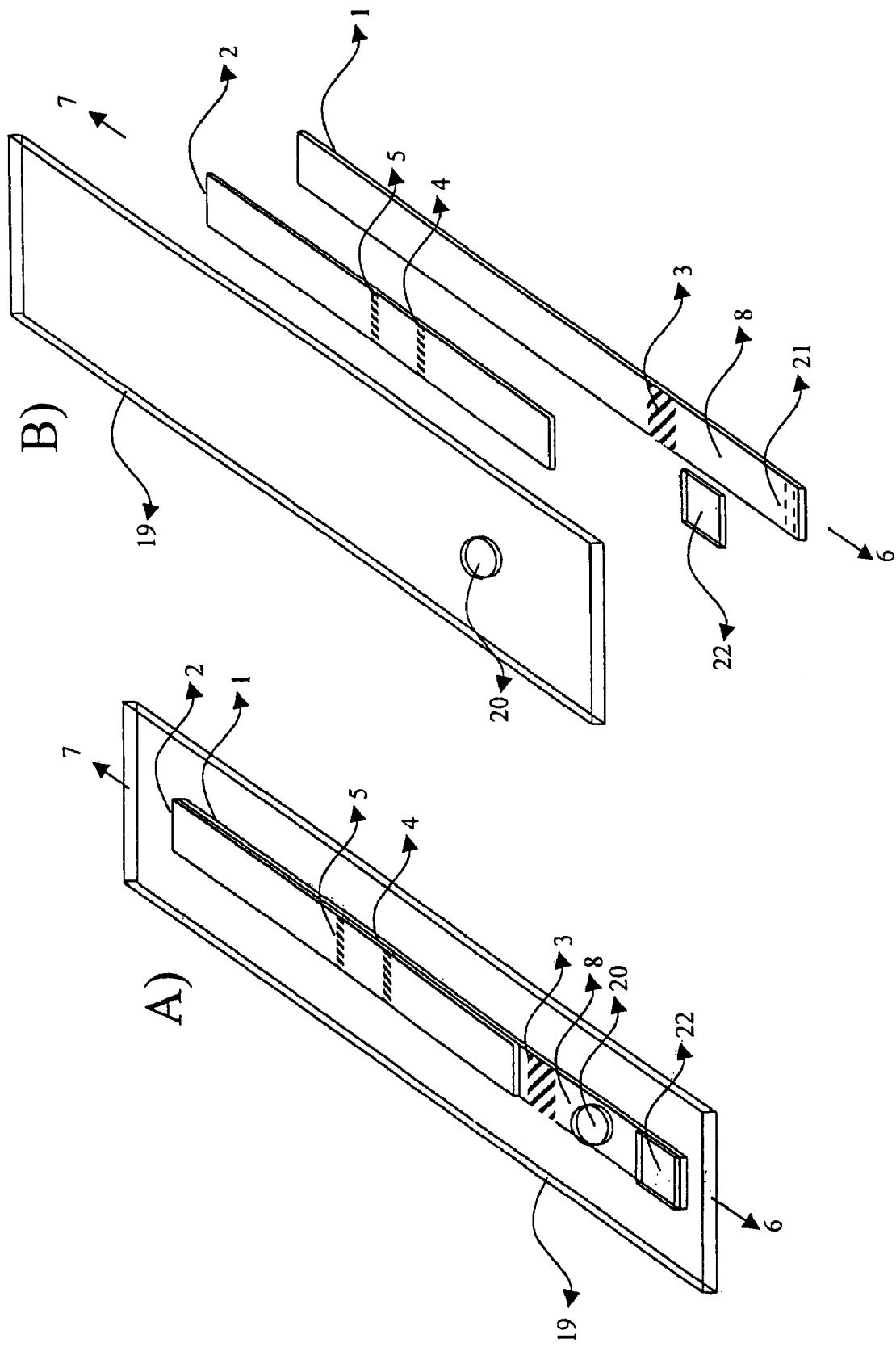
Figure 4:
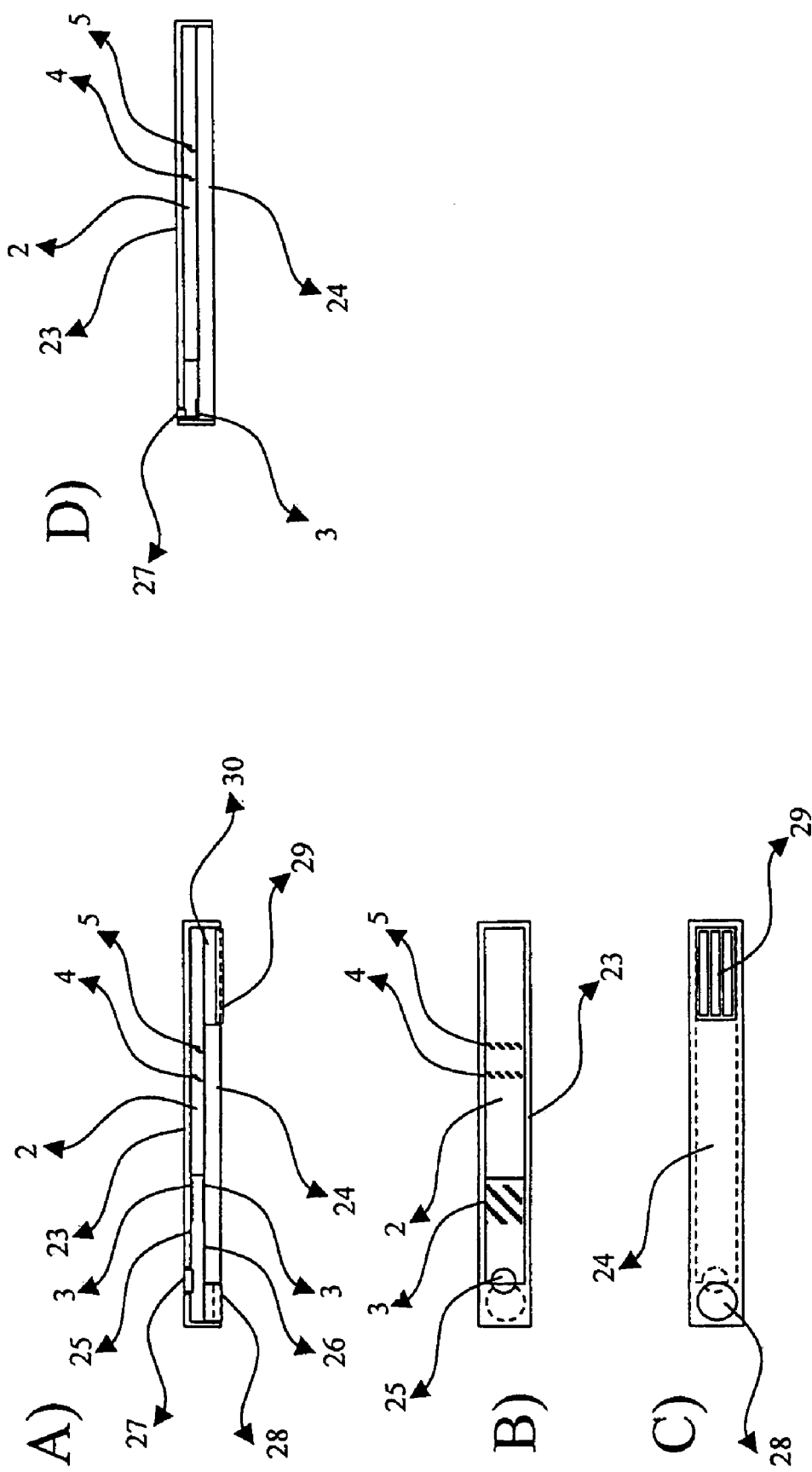
Figure 5:
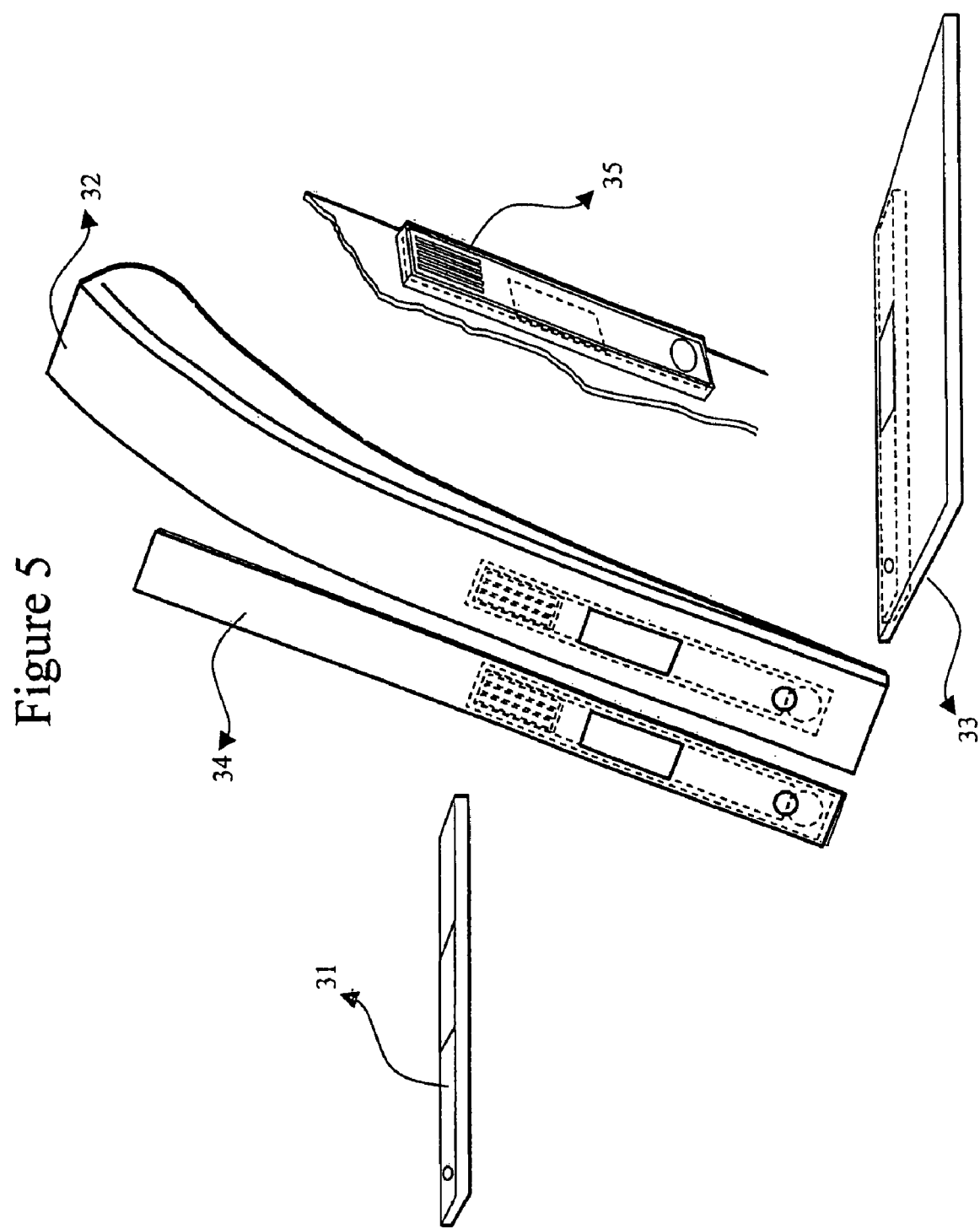

Drawing 2A shows an embodiment of the reservoir in the sampling-end of a device according to one aspect of the invention. Drawings 2B, 2C, 2D and 2E show several alternative design options for the said reservoir.

Drawing 3 shows an embodiment comprising an enlarged non-porous surface. Drawing 3A shows the assembled device, and 3B shows the unassembled unattached device.

Drawing 4A shows the one embodiment of the construction of the housing according to one aspect of the invention. Drawing 4B shows the same housing from the top and Drawing 4C shows the same housing from the bottom. Drawing 4D shows the same housing with no optional components and with an alternative placement of the labeled reagent.

Drawing 5 shows examples the accessory devices and housings according to several aspects of the invention.

Drawing 6 shows schematic diagrams of several configurations of single step assay devices as described herein which, in addition to a non-porous surface having a reversibly immobilized reagent and a porous material having an immobilized reagent, further comprise a porous sample receiving element. The reversibly immobilized reagent (1) is on the non-porous surface (2) and the irreversibly immobilized reagent(s) are in the porous material (3). Liquid sample is received by liquid sample receiving element (4).

Drawing 7A-7D shows schematic diagrams of a quantitative assay device embodying one aspect of the invention. That portion of the test strip labeled (a) contains an immobilized detection reagent (the detection zone), while (b) does not.

Drawing 8 shows a side view of a quantitative assay embodiment as described in Example 11.

DETAILED DESCRIPTION OF THE INVENTION

The invention provides a new assay platform that comprise a hybrid test strip comprising a non-porous solid surface and a porous carrier. The use of a non-porous material for the reversible immobilization of labeled reagent, which must be readily dispersed or solubilized by liquid sample application if the assay device is to function, avoids non-specific interactions that frequently interfere with such dispersal or solubilization. While not limited in usefulness to assays using particulate labels, the non-porous character of the material used for reversible immobilization avoids problems caused by particles becoming trapped within the pores of materials commonly used for reversible immobilization and the increased binding surface area of the porous media enables a higher irreversible immobilization therefore a higher signal intensity. The use of minimal number of device components decreases production related complications and the cost. The use of non-capillary liquid transport means reduces the residual liquid volume not contributing to the assay chemical reaction and the back-flow. The devices described herein are well suited for single step analyte detection, i.e., one need only apply liquid sample to the device in order to obtain a test result.

The present invention also provides improvements in quantitative, dipstick and mid-stream test device designs.

In one aspect, the reversible immobilization zone is open not only on the ends into which (inlet) and out of which (outlet) liquid sample flows, but also on one or more sides and potentially on the top. This design enhances the relative ease of manufacture. Thus, rather than being a closed system, the immobilization zone is open on at least three sides (inlet, outlet, and one side), preferably four sides (inlet, outlet and both sides), and potentially even five sides (inlet, outlet, both sides and the top, i.e., no second surface on top of the reversible immobilization zone. Further, the entire device can be open from the sides, as well as from the inlet and after the detection zone or optional sink. In addition to ease of manufacture, the openness of, for example, the distal end of the device, can permit evaporation from that end which drives the continued flow of liquid. Thus, in one aspect, the device is open on three (inlet, outlet and one side) or four (inlet, outlet and both sides) sides.

In one aspect, a single step analytical test device is provided, which produces a relevant signal depending upon the presence of a specific analyte in a liquid sample. The device comprises a non-porous solid surface and a porous carrier attached to it in fluid communication. The non-porous solid surface comprises a reversibly immobilized labeled reagent that specifically binds the analyte, located in a designated mobilization zone. The porous carrier comprises an immobilized reagent that specifically binds the analyte, located in a detection zone. The liquid sample taken into the device can initiate the mobilization of the labeled reagent, and the labeled reagent+sample mix can move to the detection zone through the porous carrier to produce the relevant signal.

In operation, the labeled reagent is not mobilized by the sample liquid passing through the porous carrier, but rather the labeled reagent dissolves or is dispersed into the liquid sample as the sample passes the non-porous surface of the mobilization zone, and is then carried into or onto the porous carrier by the liquid sample.

As noted, in the single step assay devices described herein, when liquid sample is applied to the devices described herein, that is all that is necessary to generate an assay result. However, the device can be modified to permit multi-step assay systems, such as the pre-mix of the sample and labeled conjugate before application. Furthermore, following the application of liquid sample to the device, the flow of liquid is essentially continuous. That is, the flow does not substantially stop to permit an incubation before the flow is resumed. The rate of flow can change, for example, as liquid sample moves from the non-porous solid material to the porous carrier material, but there are no impediments designed to substantially arrest the flow of the sample.

The lack of such designed impediments enables simplified and low cost production and provides an assay platform which can deliver results faster. It may also provide less complications for test performance.

In one aspect, the surface of the reversible immobilization zone is substantially smooth, i.e., the surface is not grooved or etched in order to, or in a manner that, provides increased surface area or changes the dynamics of liquid flow. A substantially smooth non-porous surface tends to release labeled reagent more efficiently than does an irregular surface containing grooves or etchings. With regard to surface area, in one aspect, the non-porous surface area occupied by the reversibly immobilized labeled reagent is minimized. While other arrangements can provide satisfactory results, in this aspect, the "footprint" of the reversibly immobilized labeled reagent is kept as small as possible. This minimizes the potential for non-specific interaction of the labeled reagent with the non-porous surface, and can provide for a more concentrated mobile label front. It can also be advantageous to locate the reversibly immobilized reagent on the non-porous surface very close to the porous carrier material. Preferably, the labeled reagent may be lyophilized or dried under vacuum in the reversible immobilization zone however, air drying of the labeled reagent is most preferred.

The devices and methods involving the novel hybrid phase (non-porous/porous) labeled reagent mobilization/detection assembly described herein can include aspects of other lateral flow assay devices well known to those of skill in the art, e.g., mobile and/or immobile control reagents, competitive assay format, etc.

In these and other aspects of the invention, the device can be contained in any housing comprising an orifice or aperture, to which a liquid sample can be introduced to initiate the assay. Such housings are known and commonly produced from water-impermeable thermoform or thermoplastic materials. As discussed elsewhere herein, the housing can play an integral role in the function of the devices in some aspects.

Another aspect of the invention relates to a reservoir structure for dip-stick tests, wherein the test strip comprises two parallel solid layers on each wide side of the strip sandwiching the porous carrier, and the said layers, by coming together, form a sample reservoir in the sampling-end of the said strip.

Another aspect of the invention relates to a device designed for mid-stream sample loading, wherein the test device comprises an enlarged outer surface with a sampling aperture. The enlarged outer surface protects the dry parts of the device from undesired wetting during the mid-stream sampling, and provides means for improved handling. A displaceable cap or shroud can optionally be included, to cover the sample application element and prevent unwanted evaporation from the sample application end of the device or to avoid damage to surfaces when the device is set down after sample loading.

In another aspect of the invention the device may be modified to perform a competition-type specific binding assay. Competition assay techniques are widely known in the prior art. Specifically the mobilizable reagent competes with the reagent (e.g. hCG antigen) in the sample for binding in the detection zone, therefore if a detectable line is present, the test is negative for the reagent (e.g. hCG antigen).

In another aspect, the devices of the invention can comprise a housing, wherein at least one element of the housing is also at least part of the non-porous solid surface comprising the mobilization zone, and the non-porous solid surface is in liquid contact with the porous carrier.

The housing according to this aspect or others described herein can be made of a single piece, or multiple pieces. The housing can be in any practical size and shape and can be made of any non-porous and non-water absorbing solid material with low affinity to the labeled reagent, including the known housings commonly produced from water impermeable thermoform or thermoplastic materials. In another aspect of the present invention the housing may be made of porous materials such as paper that is treated to become non-porous in critical areas. A porous housing can be used advantageously to absorb excess sample or can be used as a sink, in addition to adding structural integrity to the device.

In another aspect, the invention relates to accessory devices and shell housings wherein, the device in its immediate housing as described herein, can also be contained in accessory devices or shell housings.

In one aspect, the invention provides an analytical test device, which is capable of producing a relevant signal dependent upon the presence of a specific analyte in a liquid sample. Drawing 1 shows the basic construction of such a device. Drawing 1A shows the assembled device and Drawing 1B shows the unassembled device. The said device comprises a non-porous solid surface (1) and a porous carrier (2) attached to it. The said non-porous solid surface comprises reversibly immobilized labeled reagent specific for the analyte in a designated mobilization zone (3), and the porous carrier comprises an irreversibly immobilized reagent against the analyte in a designated immobilization zone (4). Optional control zone (5) also contains an irreversibly immobilized reagent.

The proximal-end (6), i.e., the wet-end, or sampling-end of the device and the distal-end (7), i.e., the dry-end of the device are also shown.

The liquid sample, introduced to the device from the proximal end can initiate, before contacting the porous carrier (2), the mobilization of the reversibly immobilized labeled reagent in the mobilization zone (3) and the label reagent-sample mix can migrate on the solid surface via porous carrier (2) to the immobilization zone through the incubation zone (9) to produce the signal and further migrate to the optional control zone (5), producing the control signal, and finally migrate to the sink zone (10).

The non-porous surface (1), can be made of any low protein binding, non-water absorbing, solid material such as thermoform or thermoplastic polymers (e.g. polystyrene, polyethylene, polycarbonate, polypropylene, fluoropolymer, or polyester, or a combination) or glass or metals or ceramics or composite materials well known to those skilled in art. The non-porous surface can also be made of any material which is surface coated with low protein binding, non-water absorbing material e.g. Teflon® fluoropolymer resins or Mylar® polyester film coated cellulose. Furthermore, the non-porous surface can be created using any material (porous or otherwise) which is capable of being compressed and or surface treated), so long as the treated surface properties are such that they do not permit liquid sample and/or the assay reagents to enter into or pass through the surface under normal assay conditions.

The porous carrier (2) can be chosen from a wide variety of commercially available porous materials, according to its flow rate, pore size, protein binding capacity, blocking requirements, suitability for a specific analyte and label, thickness and backing layer, all within the knowledge of those skilled in art. The most common types of porous carrier are nitrocellulose and porous plastics. If necessary to prevent non-specific binding or, for example, to aid in wetting properties, the porous carrier can be pre-treated with blocking agents, e.g. bovine serum albumin, or surfactants, or alternatively can be obtained pre-treated from commercial sources.

The mobilization zone (3) is essentially coated with the labeled reagent to be mobilized upon wetting. The coating can be done with a number of techniques known to those skilled in art e.g. spraying or dispensing.

Where desired, the non-porous surface, the porous surface, or both can be treated with agents (e.g., non-ionic surfactants, etc.) that modify the flow characteristics of applied liquid sample.

The immobilization zone (4) is essentially coated with the unlabeled capture reagent against the same specific analyte. The coating can be done with number of techniques known to those skilled in art e.g. spraying or dispensing. Depending upon the methods used, the coating will result in varying degrees of penetration of the immobilized reagent into the porous carrier. Such penetration is neither required for nor detrimental to the function of the devices described herein. That is, there is generally no negative impact of such penetration, although it can be desirable, e.g., to provide a higher concentration of immobilized reagent in a smaller area. The most common method of permanently binding the capture reagent to the immobilization zone, is passive absorption e.g. dispensing/spraying, incubating, and drying an aqueous reagent solution on the porous carrier.

Optionally, the immobilization zone of the porous carrier can be compressed, to slow down the liquid flow and increase the immuno-concentration, thus increasing the signal strength. The compression of the porous carrier in the immobilization zone can be performed prior to or simultaneously with the application of the capture reagent.

The porous carrier (2) has two basic functions, to regulate the migration of the liquid sample+the labeled reagent mix, and to comprise the immobilization zone (4) and optionally the control zone (5).

Incubation between the analyte (if present) and the labeled reagent takes place partly in the mobilization zone (3) and partly through the migration between mobilization and immobilization zones. Therefore, liquid passage time between the mobilization zone (3) and the immobilization zone (4) through the incubation zone (9) has an effect on the sensitivity of the device. It is known that by adjusting the length of the incubation zone (9) and the flow rate of the porous carrier, the sensitivity of the device can be altered.

The distal portion of the porous carrier after the optional control zone (5) acts as a liquid sink (10).

In a preferred embodiment, the device also comprises a sample reception zone (8) on the non-porous solid surface (1), comprising sample treatment reagents, either to be mobilized instantly when wet (e.g. surfactants, salts, pH agents, blockers) or binding agents for molecules to be blocked from the test system. The treatment agents can additionally, or in the alternative, be applied to the porous carrier.

In a preferred embodiment, the device also comprises an optional zone (13) and an optional attachment zone (21) on the non-porous carrier, which can be used for production and assembly purposes. The optional zone (13) can also comprise wetting agents, such as non-ionic surfactants to promote the liquid migration to within the porous carrier.

In a preferred embodiment, the device comprises a second non-porous surface (11) which is attached parallel to the first non-porous surface (1), to enhance the sample application and/or the liquid sample transport from the optional sample reception zone (8) to the proximal end (14) of the porous carrier and/or to avoid the surface transport over the porous carrier (2) and to avoid premature drying of the liquid sample and/or to improve the robustness of the device.

In a preferred embodiment, the second non-porous surface (11) is shorter than the first non-porous surface (1) to expose the optional sample application zone (8) and to create guidance to the sample application, in the proximal-end of the device.

In a preferred embodiment, the second non-porous surface (11) or the first non-porous surface (1) is shorter than the other one in the distal-end (7) of the device subject to the invention. Thus exposing a part of the liquid sink (10) to the atmosphere, therefore creating an evaporation surface, enhancing the liquid absorption capacity of the sink (10) and inhibiting backflow of the liquid sample.

In a preferred embodiment, the inner surface (communicating with the porous carrier) of the second non-porous surface (11) also comprises a mobilization zone (16) together with the mobilization zone (3) on the first non-porous surface (1) or instead of the zone on the first surface. The same is possible between the sample reception zone (15) on the second non-porous surface (11) and the sample reception zone (8) on first non-porous surface (1). It is additionally preferred that when the second non-porous surface bears the mobilization zone, the second non-porous surface is above the first non-porous surface during operation of the device, such that gravity also aids in mobilizing the labeled reagent into the solution.

In a preferred embodiment, the test device as shown in Drawing 1 is assembled into a housing made of various materials such as thermoformed or molded plastic materials. Such housing materials and designs are well known to those skilled in art.

Another aspect of the invention concerns a reservoir structure for dip-stick tests, wherein the test strip comprises two parallel solid layers on each wide side of the strip sandwiching the porous carrier and the said layers, that, by coming together, form a sample reservoir in the sampling-end of the said strip.

As shown in Drawing 2A, both non-porous surfaces (1 and 11) are attached to the each other or are the continuation of the each other or overlap each other, at the proximal-end (6) of the device subject to the invention, therefore creating a reservoir (17) for the sample. The reservoir (17) can collect the required amount of the liquid sample instantly, thus eliminating the need to dip the device for a measured time into a liquid sample. The reservoir (17) can be designed in any of a number of shapes, from bulbous to angular; some alternatives are shown in un-scaled side views in Drawings 2B, 2C, 2D and 2E. The reservoir (17) can also comprise substances similar to that of the optional sample reception zone (8).

In a preferred embodiment, the reservoir (17) comprises an orifice (18) on either of the non-porous solid surfaces, which can provide means for sample dispensing and ventilation to release the liquid sample from the reservoir (17).

Another aspect concerns a device optimized for midstream sample collection, wherein the test device comprises an enlarged surface with a sampling orifice. The said enlarged surface protects the dry parts of the device from undesired wetting during the mid-stream sampling and providing means for improved handling.

As shown in Drawing 3, as an assembled device in Drawing 3A and as an unassembled device in 3B, the second non-porous surface is sized wider and longer (19) than the first non-porous surface (1), thus providing improved handling and protection from undesired wetting in mid-stream sample application. In such a device design, the sample is taken to the sample reception zone (8) through the orifice (20) on the enlarged non-porous surface (19).

In a preferred embodiment, the enlarged second non-porous surface (19) can be attached to the optional attachment zone (21) in the distal end of the first non-porous surface and to the porous carrier (2) on the upper surface of the porous carrier. An optional spacer (22) can be used to maintain an even distance between the surfaces through the sample reception zone (8).

In a preferred embodiment, a third layer can be attached to a device with normal sized non-porous surfaces (Drawing 1 and 2) in the same manner.

Another aspect, concerns a housing, wherein at least one element of the housing is also part of the non-porous solid surface comprising the mobilization zone. In this aspect, as in the first aspect, the said solid surface is in liquid contact with the porous carrier.

The housing subject to invention can be made of a single piece or multiple pieces. The housing can be in any practical size and shape and can be made of any non-porous and non-water absorbing solid material with low affinity to the labeled reagent including the known housings commonly produced from water impermeable thermoform or thermoplastic materials. However, it is further possible to have a porous housing made non-porous in critical areas such that the porous nature of the housing can advantageously be used to absorb the excess applied sample or can be used as a sink.

The device with housing shown in see-through side view in Drawing 4A is composed of a top (23) and a bottom (24) housing parts and a porous carrier (2). The inner surfaces (25 and 26) of both or either parts comprise the mobilization zone (3). The liquid sample is taken into the device through the intake orifice (27). The excess of liquid taken into the device is drained out through the optional drain orifice (28). The inner surfaces (25 and 26) between the intake orifice (27) and the mobilization zone (3) are the sample reception zone. There can be an optional evaporation grill (29) on the distal bottom end of the device, to assist the sink function. The porous media can, optionally be folded over itself (30), to create a shorter device design, without decreasing the sink capacity.

Drawing 4B shows the same device from the top and Drawing 4C shows the same device from the bottom. Drawing 4D shows in see-through side view, the same housing without optional drain orifice (28), and other optional components, e.g. folded porous carrier (30) or evaporation grill (29). Also shown in Drawing 4D is an alternative placement of the mobilization zone (3).

Another aspect concerns accessory devices and shell housings wherein the device in immediate housing or in other words, a primary housing, subject to the invention can also be contained in accessory devices or shell housings, in other words, secondary housings.

Drawing 5 shows examples of such an adaptation, wherein the device with an immediate housing (Drawing 4) is contained in a molded plastic shell for home use (32) or on/in a dip stick extender (34) or in a bench top device (33) or used as it is (31). Adaptation can be achieved by a simple receptacle slot (35) in the accessory device as an example shown (35) in cut-away view from inside of any of these accessory devices.

For all aforementioned devices, it will be apparent to those skilled in art that, to enable signal observation, either or both sides of the signal producing zones should be transparent or should comprise means to enable the observation of the test result e.g. a window, and all above mentioned solid parts, non-porous or porous can be attached to each other by known techniques such as ultrasonic welding, hot laminating, adhesives or mechanical means.

EXAMPLES

1. Non-porous Solid Surface Material:

The non-porous solid surface can be chosen from wide variety of materials e.g. polystyrene, polyethylene, polycarbonate, polypropylene, or polyester, or a combination, available from numerous commercial sources e.g. General Electric, USA in sheets in a variety of forms and thicknesses.

2. Porous Carrier:

The porous carrier can be chosen from a wide variety of chromatographic materials e.g. cellulose, nitrocellulose or porous plastic, available from numerous commercial sources e.g. Whatman, UK; Schleicher & Schuell, Germany and Porex, USA. Non-limiting examples include hydrophilic porous polyethylene membrane, for example with pore size between 2 and 8 micrometer, or lateral flow test nitrocellulose membrane.

3. Label Material:

The label can be chosen from wide variety of materials commonly known to those skilled in art, e.g. metals, dyes, polymers, enzymes and fluorophores. Use of colloidal gold and latex polymer particles are the most common.

Colloidal gold can be obtained from commercial sources e.g. BBI, UK. The gold particles can also be produced, for example, according to U.S. Pat. No. 4,313,734. As an example, colloidal gold particles of approximately 40 nm in diameter can be used.

Polymer particles can be obtained from numerous commercial sources commonly known to those skilled in art e.g. Bangs Laboratories, USA.

4. Binding Reagents:

The binding reagents may be antigens, antibodies or other binding partner arrangements (Avidin-Biotin). Antibodies may be useful as binding reagents, and can be monoclonal or polyclonal obtained from numerous commercial sources, commonly known to those skilled in art. Alternatively, antibodies can be raised to a desired antigen according to methods well known in the art.

Labeling and capture antibodies can be obtained, for example from Medix, Finland (clone codes: 5006 and 6601) for hCG in case of a pregnancy test.

A control antibody against the labeling antibody, for example, can be obtained from Dako, Denmark (code: Z 0109).

It should be understood that while antibodies (or, for example, antigen-binding fragments of antibodies) are preferred binding reagents, the binding reagents can be selected from any reagent that binds or specifically binds the analyte of interest. Thus, agents such as nucleic acids, including, but not limited to aptamers, as well as specific binding partners, e.g., a polypeptide with a complementary binding domain for a target protein, such as a leucine zipper or SH2 domain, are candidates for use in devices and methods as described.

5. Conjugation of Antibody to a Label:

Conjugation of antibody to a label is a common practice to those skilled in art described, e.g. in U.S. Pat. No. 4,313,734 or U.S. Pat. No. 5,571,726. Gold conjugates can be prepared by the adsorption of antibody to the gold surface within minutes through charge attraction, hydrophobic attraction, or sulfur binding.

Polymer conjugates can be prepared by adsorption or covalent binding of antibodies to the particles according to known methods e.g. Bangs Laboratories TechNotes 204 (adsorption to microspheres), 205 (covalent coupling), and 303 (lateral flow tests).

Alternatively pre-conjugated antibodies can be obtained from numerous commercial sources e.g. Arista, USA, and British Biocell, UK.

6. Reversible Immobilization of Labeled Antibody to the Non-porous Solid Surface:

Reversible immobilization solution was obtained from British Biocell, UK, and contained 40 nm colloidal gold coated with anti hCG antibodies at optical density 10. If desired, solubilizing agents such as trehalose (Sigma, T-5251) can be added to the reversible immobilization solution.

1 microliter of this solution was dispensed per mm width of the solid surface, to the designated mobilization zone (3) on non-porous surface. Drying was done in room temperature under 20% relative humidity, over night.

Stabilizing systems or buffers for mobilizable dried reagents are known (see, e.g., Brooks et al., 1986) and are also commercially available (e.g., from Surmodics, U.S.A.). The use of such buffer systems can enhance the stability of labeled reagents in the dry state and can improve the mobilization characteristics of such reagents.

The non-porous surface material used was a transparent polycarbonate sheet of 200 micrometer thickness. The sheet was cut into strips of 5 mm width in varying lengths.

7. Immobilization of Unlabeled Antibodies onto the Porous Carrier:

Monoclonal antibody solution against the alpha-subunit of hCG at 5 mg/ml was dispensed at 0.2 microliter/per mm width of the porous carrier onto the designated immobilization zone (4) in surfactant-treated porous carrier and dried at room temperature under 20% relative humidity, overnight.

Anti-mouse control antibody was also immobilized using the same protocol.

The porous member can be treated with surfactants or other wetting, blocking or optimizing agents if desired.

8. Assembly:

The transparent non-porous solid surface was cut in the shape of a rectangular strip of 55 mm×5 mm. From the proximal end, at the 10th millimeter to 55th mm the porous carrier (5×45 mm) was attached using water-resistant double-sided transparent adhesive tape. A second non-porous solid surface was cut into a strip of 5×60 mm and attached to the porous carrier, parallel to the first non-porous surface, using adhesive tape.

Thus, the structures shown in Drawing 1 were achieved.

In another assembly format, the transparent non-porous solid surface was in the shape of a rectangular strip of 121 mm to 5 mm. From the distal end to the 45th millimeter the porous carrier similar to the previous assembly was attached using water-resistant double-sided adhesive tape. Between the 60th and 61st millimeters the solid surface was bent twice at 90 degrees and was attached to the porous carrier using water-resistant double-sided adhesive tape.

Thus, the structure similar to what is shown in Drawing 2A was achieved.

In another assembly format, the transparent non-porous solid surface was cut in the shape of a rectangular strip of 70 mm by 5 mm. From the proximal end, 25th millimeter to 70th millimeter, the coated porous carrier was attached using water-resistant double-sided adhesive tape.

A second transparent non-porous solid surface, made of the same material, was cut in a rectangular shape of 120 mm by 50 mm. From the proximal end, a hole of 3 mm diameter was punched between the 12th and 15th millimeters on the longitudinal axis. Using double-sided tape over the porous carrier and on the proximal 5 mm of the aforementioned strip structure, the strip structure was attached to the under side of the rectangular sheet, in such a way that the sample receiving zone of the strip was exposed through the hole.

Thus, the structure shown in Drawing 3 was achieved.

9. Assay for hCG:

To test the function and sensitivity of the assay kits as disclosed herein, a lyophilized hCG standard (calibrated against World Health Organization International Standard 75/537) was diluted in PBS. 20 to 80 microliters of freshly-prepared hCG dilutions (20 IU hCG/l, 100 IU/l, 2000 IU/l, and 20000 IU/l) were pipetted to the sample reception zone of the device for each of 96 identical devices (total of 384 devices used for hCG dilutions). As a control, 80 microliters of PBS were pipetted to another 20 devices.

All devices with PBS and 20 IU hCG/l gave no visible positive signal.

All devices with 100 IU/l hCG/l or higher gave visible positive signal.

It is noted that the devices described herein have sensitivity effective for diagnosis of pregnancy at its earliest stages.

10. Devices Including a Porous Sample Receiving Element.

In one aspect, devices embodying the non-porous/porous hybrid phase assembly described herein can include a porous sample-receiving element as shown in Drawing 6. Referring to the drawing, in one embodiment, the assembly includes a non-porous surface (2) upon which labeled reagent (1) is reversibly immobilized, adjacent to a porous carrier material (3) that can be attached to the non-porous surface (2). A porous sample-receiving material (4), e.g., filter paper, such as Whatman paper or a porous plastic material or other materials commonly used as sample application pad materials for lateral flow assay devices, is placed such that it overlaps or abuts with the non-porous surface. Several different arrangements with regard to the placement of the sample-receiving element and the reversibly immobilized reagent are shown in panels A-D of Drawing 6. As shown in Drawing 6A, the porous sample-receiving material can overlap the reversibly immobilized labeled reagent (1). Alternatively, as shown in Drawing 6B, the porous sample-receiving element (4) can overlap both the reversibly immobilized labeled reagent (1) and the porous carrier material (3). In another alternative, shown in Drawing 6C, labeled reagent (1) is reversibly immobilized on the non-porous surface (2), the porous carrier material (3) overlaps the reversibly immobilized labeled reagent (1), and the porous sample receiving element (4) overlaps the porous carrier material (3). In yet another alternative, depicted in Drawing 6D, the labeled reagent (1) is reversibly immobilized on the non-porous surface (2) adjacent to, and preferably, abutting or in contact with the porous sample receiving element (4) on one (upstream) side and the porous carrier material (3) on the other (downstream) side.

11. Quantitative Assay Format:

In another aspect, a quantitative lateral flow assay is provided. In this aspect, rather than immobilizing a capture reagent in a relatively narrow discrete line perpendicular to the flow of the liquid sample, the non-reversibly immobilized reagent is applied in a larger detection area, longitudinal and parallel to the direction of liquid flow. Examples are depicted in Drawing 7, in which the detection zone, comprising the non-reversibly immobilized capture reagent is applied essentially to the length of a porous material, which is one option (it is important to note that there is no requirement, according to this aspect, that the detection area span the entire length of the porous material).

The detection area is coated with non-labeled reagents as used in the detection zones of qualitative assay devices as described herein, but preferably in lesser concentration and over a larger area, i.e., not in a narrow line. The labeled reagents useful in this assay format are the same as would be used in the qualitative assay formats.

The detection area can cover the entire width of the material, as shown in Drawing 7B, or, alternatively, just a strip on the material, as shown in Drawing 7A, (a). Where the arrangement of Drawing 7A is desired, it can be achieved, for example, by making the remainder of the membrane (b) hydrophobic or non-porous, which thereby directs the flow of liquid sample into a narrow strip. This arrangement can increase the flow, and thus, the immuno-concentration on the longitudinal (strip-like) detection area.

The detection arrangement described above and depicted in Drawings 7A-7D can be incorporated into an assay device comprising a reversibly immobilized, labeled reagent either as described herein (reversibly immobilized on a non-porous surface) or as is known in the art (for example, reversible immobilization on the chromatographic material, e.g., through use of a glazing material, e.g., a sugar, protein or polymer, or reversible immobilization in a material such as a glass fiber filter or porous plastic which releases particulate label more readily than the chromatographic material used in the detection area, among others). While particulate labels are preferred, devices according to this aspect, like the others described herein, are not limited to the use of particulate labels. Alternative labels can include, for example, dyes, such as fluorescent dyes, enzymes, isotopes, etc.

In use, following the application of liquid sample which mobilizes reversibly immobilized labeled reagent (e.g., particle labeled antibody against the analyte), the labeled reagent, complexed with analyte, if present, migrates onto the detection area. Labeled reagent-analyte conjugate will be trapped by the immobilized detection reagent (e.g., a second antibody that binds the analyte) as the conjugate migrates over or through the detection zone. The conjugate will tend to bind the immobilized detection reagent in the proximal region of the detection area (that region first coming in contact with the liquid sample carrying the conjugate) first, giving a detectable signal. Quantitation is achieved based on how far distal to that first proximal region the signal is detected above background. That is, as the immobilized reagent in the proximal detection area is saturated for binding, unbound conjugate will continue along the detection zone until free immobilized detection reagent is encountered. The more analyte present, the further along the detection area (distally) the signal will be detected. This is depicted schematically, for example, in Drawing 8. As an example, gold-conjugated anti-hCG, bound to hCG present in the sample, is trapped by proximal capture antibodies first, and how far distally the color signal goes will depend purely on the concentration of the analyte in the sample.

To aid in interpretation, the detection area for the quantitative embodiments can be, for example, graduated, as shown in Drawing 7C, or it can contain a cut-off point as shown in Drawing 7D. Alternatively, or in addition, the detection area can be arranged as successive parallel lines of unlabeled binding reagent, each separated by a small gap, such that the detection area is graduated, permitting quantitation of analyte based upon the number of lines showing bound label. Assays in the quantitative format can, of course, also contain a control reagent zone as used in other lateral flow assay devices.

Additional aspects of the devices described herein enhance the ability to obtain quantitative results. For example, the reservoir designs discussed herein above can provide a fixed volume of sample. The fixed volume permits uniform sampling, which aids in reliable quantitation of analyte. Without a fixed volume of sample, quantitation can be, at best, semi-quantitative. In contrast, measurement of a fixed volume permits true quantitation.

Further, because the non-porous surface does not retain a dead volume of sample, essentially all of the applied sample (e.g., essentially all of a fixed volume of sample) is transferred to the porous carrier material wherein detection of analyte can occur. Where there is a dead volume of liquid sample, for example in kits which comprise a porous sample application element or a porous conjugate release element, the amount of liquid sample retained, and thus not measured for analyte, can vary from assay to assay, in a manner that does not occur when a reservoir as described herein is employed. It is noted that the space between upper and lower sheets of non-porous material as employed in several embodiments described herein is also a fixed volume reservoir, i.e., the device does not necessarily have to have a reservoir formed by bending one non-porous surface over on itself as also described.

In addition, the reservoir designs, coupled with the non-porous nature of the zone in which the labeled reagent is temporarily immobilized, also provide a fixed volume for labeled reagent release, resulting in a fixed concentration of labeled reagent that does not result in assays that lack such a fixed volume reservoir. This design further enhances the ability to obtain reliable quantitative results.

The reservoir designs described herein provide a further benefit with regard to quantitative assays in that the filling of the reservoir, e.g., by dipping vertically into a liquid, does not necessarily start the assay. In one aspect, for example, the reservoir can be designed such that the surface of the liquid, when the reservoir is full and the device is in the vertical position, is separated from the porous carrier strip and/or from the reversible immobilization zone. In this aspect, only when the device is laid horizontal does the liquid sample migrate across the reversible immobilization zone and enter the porous carrier strip. Thus, such a reservoir design can permit closer control of the timing of the assay when this is critical, because the assay does not begin until the device is laid horizontal.

It is to be understood that the measurement of analytes in addition to hCG are encompassed by the devices and methods described herein, including, but not limited to other hormones (e.g., leuteinizing hormone (LH), follicle stimulating hormone (FSH), thyroid stimulating hormone (TSH), insulin, pancreatic glucagon and its fragment peptides, parathyroid hormone, calcitonin, adrenocorticoid hormones, growth hormone, etc.), proteins (e.g., viral, fungal or bacterial antigens, antibodies, alphafetoprotein, carcinoembryonic protein, enzymes, PSA, etc.) and chemical analytes such as clinical chemistry analytes and drugs (including, but not limited to drugs of abuse, e.g., cocaine, heroin, other narcotics, and steroids) and drug metabolites, toxins, etc. That is, the devices described herein can be adapted by one of skill in the art, given specific binding reagents for the particular analyte, for the identification of such analytes in liquid samples.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

The invention claimed is:

1. An analytical device for a single-step determination of the presence of an analyte in a liquid sample, comprising:
   a non-porous solid surface comprising a sample reception zone and, in a reversible immobilization zone, a reversibly immobilized labeled reagent that binds said analyte to form a complex, and
   a porous carrier comprising, in a detection zone, an immobilized reagent that binds said complex in the presence of analyte to generate a detectable signal, wherein said porous carrier is in contact with said non-porous surface.

2. The device of claim 1 further comprising a sink, distal to and in contact with said porous carrier, said sink capable of absorbing excess liquid sample after said liquid sample traverses said test strip.

3. The device of claim 1, wherein said porous carrier further comprises, a control site separate from and distal to the detection zone.

4. The device of claim 3 wherein said reversible immobilization zone comprises a plurality of labeled reagents.

5. The device of claim 4 wherein each of said plurality of labeled reagents binds a different analyte.

6. The device at claim 4 wherein said porous carrier comprises, in one or more detection zones, a plurality of immobilized binding reagents.

7. The device of claim 6 wherein each of said plurality of immobilized binding reagents is located in a spatially distinct detection zone and each binds a different analyte to generate a detectable signal.

8. The device of claim 1 which further comprises a plurality of said test strip assemblies, each assembly bearing reagents that identify the presence of one or more different analytes.

9. The device of claim 1 which further comprises a second non-porous solid surface, said surface is sized such that when said second non-porous solid material is placed over said first non-porous surface, no edge of said first non-porous surface extends beyond an edge of said second non-porous surface, wherein said second piece of non-porous solid surface is positioned parallel to said first non-porous surface, said second piece having an aperture through which sample is introduced, and wherein said second piece is positioned such that said aperture is located upstream of said reversible immobilization zone and provides protection to said first non-porous surface from undesired wetting during sample application.

10. The device of claim 1 further comprising a sample reservoir, proximal to said reversible immobilization zone and formed from a continuation of said nonporous solid surface or from the juxtaposition of a second non-porous solid surface with said first non-porous solid surface.

11. The device of claim 1, further comprising a housing.

12. The device of claim 11, wherein at least one element of said housing comprises the non-porous solid surface.

13. The device of claim 11, further comprising a sink, distal to and in contact with said porous carrier, said sink capable of absorbing excess liquid sample after said liquid sample traverses said test strip, and wherein said housing comprises an aperture to permit evaporation from said sink.

14. The device of claim 11, wherein said housing comprises an aperture through which sample is applied and an aperture through which a result is observed.

15. The device of claim 14, wherein said observation aperture is covered by a non-porous transparent material.

16. The device of claim 15 wherein said reversible immobilization zone is open on at least three sides.

17. The device of claim 1, wherein the detection zone is at the proximal end of the porous carrier.

18. The device of claim 1, wherein the label is a colloid, a dye, a latex particle, an enzyme or a fluorophore.

19. The device of claim 1, wherein the non-porous solid surface is glass, a metal, a ceramic, a high surface density plastic, a polymer, a fluoropolymer resin, or polyester film.

20. The device of claim 1, wherein the porous carrier is nitrocellulose or paper.

21. A method of detecting an analyte, the method comprising
   a) contacting a liquid sample to be tested for said analyte with the analytical device of claim 1; and
   b) permitting said liquid sample to traverse said test strip such that said reversibly immobilized labeled reagent is mobilized by the sample and flows to said detection zone, wherein, if analyte is present in said liquid sample, a detectable signal is generated indicative of the presence of said analyte.

22. An analytical device for the determination of an analyte in a liquid sample, comprising:
   a non-porous solid surface comprising a sample reception zone and, in a reversible immobilization zone, a reversibly immobilized reagent able to be mobilized with the passing liquid sample; and
   a porous carrier comprising, in a detection zone, an immobilized reagent that generates a detectable signal in the presence or absence of analyte, wherein said porous carrier is in contact with said non-porous surface.

* * * * *

UNITED STATES PATENT AND TRADEMARK OFFICE
CERTIFICATE OF CORRECTION

PATENT NO. : 7,632,687 B2  Page 1 of 1
APPLICATION NO. : 11/088579
DATED : December 15, 2009
INVENTOR(S) : Cem Gokhan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this

Second Day of November, 2010

David J. Kappos
*Director of the United States Patent and Trademark Office*